United States Patent
Rath et al.

(10) Patent No.: US 9,035,085 B2
(45) Date of Patent: May 19, 2015

(54) ARYL KETONE COMPOUNDS AND COMPOSITIONS FOR DELIVERING ACTIVE AGENTS

(75) Inventors: Parshuram Rath, Yorktown Heights, NY (US); Maria Isabel Gomez-Orellana, New Rochelle, NY (US)

(73) Assignee: EMISPHERE TECHNOLOGIES, INC., Roseland, NJ (US)

( * ) Notice: Subject to any disclaimer, the term of this patent is extended or adjusted under 35 U.S.C. 154(b) by 0 days.

(21) Appl. No.: 12/045,395

(22) Filed: Mar. 10, 2008

(65) Prior Publication Data

US 2008/0167217 A1 Jul. 10, 2008

Related U.S. Application Data

(63) Continuation of application No. 11/568,830, filed as application No. PCT/US2005/017339 on May 16, 2005, now abandoned.

(60) Provisional application No. 60/571,090, filed on May 14, 2004, provisional application No. 60/571,092, filed on May 14, 2004.

(51) Int. Cl.
C07C 303/00 (2006.01)
C07C 233/33 (2006.01)
A61K 31/192 (2006.01)
A61K 45/06 (2006.01)
C07C 59/90 (2006.01)

(52) U.S. Cl.
CPC ............. *C07C 233/33* (2013.01); *A61K 31/192* (2013.01); *A61K 45/06* (2013.01); *C07C 59/90* (2013.01)

(58) Field of Classification Search
None
See application file for complete search history.

(56) References Cited

U.S. PATENT DOCUMENTS

| | | | |
|---|---|---|---|
| 2,447,998 A | 8/1948 | Clapp | |
| 3,046,301 A | 7/1962 | Phillips et al. | |
| 3,720,690 A | 3/1973 | King et al. | |
| 3,784,701 A * | 1/1974 | Tomcufcik et al. | 514/570 |
| 4,407,757 A * | 10/1983 | Morimoto et al. | 554/218 |
| 4,421,685 A | 12/1983 | Chance et al. | |
| 4,544,565 A * | 10/1985 | Barnett | 426/538 |
| 5,401,516 A | 3/1995 | Milstein et al. | |
| 5,443,841 A | 8/1995 | Milstein et al. | |
| 5,474,978 A | 12/1995 | Bakaysa et al. | |
| 5,534,488 A | 7/1996 | Hoffmann | |
| 5,629,020 A | 5/1997 | Leone-Bay et al. | |
| 5,643,957 A | 7/1997 | Leone-Bay et al. | |
| 5,766,633 A | 6/1998 | Milstein et al. | |
| 5,776,888 A | 7/1998 | Leone-Bay et al. | |
| 5,866,536 A | 2/1999 | Leone-Bay et al. | |
| 6,888,033 B1 * | 5/2005 | Arad et al. | 568/335 |
| 2002/0141985 A1 | 10/2002 | Pittner et al. | |
| 2003/0194443 A1 * | 10/2003 | Yano et al. | 424/497 |
| 2005/0113366 A1 * | 5/2005 | Bourguignon et al. | 514/221 |
| 2006/0035970 A1 * | 2/2006 | Hodge et al. | 514/543 |

FOREIGN PATENT DOCUMENTS

| | | |
|---|---|---|
| EP | 0156317 | 10/1985 |
| EP | 0191724 | 8/1986 |
| WO | WO-9310677 A1 | 6/1993 |
| WO | WO-9612473 A1 | 5/1996 |
| WO | 96/30036 | 10/1996 |
| WO | WO-9635418 A1 | 11/1996 |
| WO | 98/20885 | 5/1998 |
| WO | 98/49135 | 11/1998 |
| WO | 00/06534 | 2/2000 |
| WO | 00/07979 | 2/2000 |
| WO | 00/40203 | 7/2000 |
| WO | 00/47188 | 8/2000 |
| WO | 00/50386 | 8/2000 |
| WO | 00/59863 | 10/2000 |
| WO | 01/32130 | 5/2001 |
| WO | 01/32596 | 5/2001 |
| WO | 01/44199 | 6/2001 |
| WO | 01/51454 | 7/2001 |
| WO | 02/02509 | 1/2002 |
| WO | 02/15959 | 2/2002 |
| WO | 02/16309 | 2/2002 |
| WO | 02/19969 | 3/2002 |
| WO | 02/20466 | 3/2002 |

(Continued)

OTHER PUBLICATIONS

Levrand et al., Photochem. Photobiol. Sci., 2002, 1, 907-919.*

(Continued)

*Primary Examiner* — Karl J Puttlitz

(74) *Attorney, Agent, or Firm* — Blank Rome LLP

(57) ABSTRACT

The present invention provides aryl ketone compounds and compositions containing them which facilitate the delivery of active agents. The aryl ketone compounds have the formula

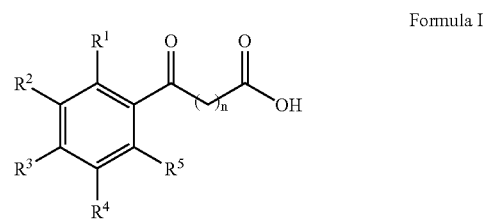

Formula I or a salt thereof, where n=1 to 9, and $R^1$ to $R^5$ are independently hydrogen, $C_1$ to $C_4$ alkyl, $C_1$ to $C_4$ alkoxy, $C_2$ to $C_4$ alkenyl, halogen, hydroxyl, —NH—C(O)—$CH_3$, or —O—$C_6H_5$.

13 Claims, No Drawings

(56) References Cited

FOREIGN PATENT DOCUMENTS

| WO | 02/47712 | | 6/2002 |
|---|---|---|---|
| WO | 02/069937 | | 9/2002 |
| WO | WO-02068442 | A1 | 9/2002 |
| WO | 03/045306 | | 6/2003 |
| WO | 2005117854 | * | 12/2005 |

OTHER PUBLICATIONS

Kawamatsu et al., Cent. Res. Div., Takeda Chem. Ind., Ltd., Osaka, Japan.*
Database CAS citation 1997:563086 for WO 9730017 [retrieved Nov. 9, 2009] from STN; Columbus, OH, USA.*
Database CAPLUS Chemical Abstracts Service, Columbus, Ohio, US; Database Accession No. 2001:47921, Abstract of Sikkandar: Asian Journal of Chemistry (2000), 12(4), 1337-1338.*
Masse et al., Applied and Environmental Microbiology (1984), 47(5), 947-51.*
"Antigens and Immunogens" in Atlas of Immunology, Second Edition Julius M. Cruse and Robert E. Lewis CRC Press 2003.*
"Vitamins, Survey" in Kirk-Othmer Encyclopedia of Chemical Technology, John W. Scott Published Online: Dec. 4, 2000, DOI: 10.1002/0471238961.1921182219031520.a0, Copyright © 2001 by John Wiley & Sons, Inc., pp. 1-11.*
Levrand et al., Light induced control release of alkyl phenyl ketones, Photochemical & Biological Sciences (2002), vol. 1, No. 11, pp. 907-191, CAPLUS (online) Columbus, OH, USA, Chemical Abstracts (retrieved on May 24, 2006).
Database CA (Oniine). Chemical Abstracts Service, Columbus, Ohio. US. Treibs, W. et al; "Syntheses with di-carboxylic acids. VI. The Fries' rearrangement of esters of dicarboxylic acids" XP002426698 retrieved from STN Database accession No. 49:23600, 1954.
Database CA [Online] Chemical Abstracts Service, Columbus, Ohio, US: Fujita, A. et al: ".omega. Cyclic fatty acids. III. Syntheses of some hydroxyaroyl and hydroxyaryl fatty acids" XP002426699 retrieved from STN Database accession No. 50:69243, 1995.
Levrand B et al: "Light Induced Control Release of Fragances by Norrish Type II Photofragmentation of Alkyl Phenyl Ketones" Photochemical and Photobiological Sciences, Royal Society of Chemistry, Cambridge GB, vol. 1, No. 11, 2002, pp. 907-911, XP008071646 ISSN: 1474-905X, 2002.
Fujita, et al., Studies on ω-Cyclic Fatty Acids, III. Synthesis of some Hydroxyaroyl- and Hydroxyarylfatty Acids, U.D.C. 615.778.47:547.29, 1955.
Tomico, et al., Synthesis and Antibacterial Activity of o- or p-Substituted Phenol Derivatives, UDC 547.563.1:576.851.5.095.18, 1958.
Triebs, et al., Synthesen mit Dicarbonsauren (VI) 139624: pp. 345-349, 1954.

* cited by examiner

ARYL KETONE COMPOUNDS AND COMPOSITIONS FOR DELIVERING ACTIVE AGENTS

CROSS-REFERENCE TO RELATED APPLICATIONS

This application is a continuation of U.S. application Ser. No. 11/568,830, filed Nov. 8, 2006. U.S. application Ser. No. 11/568,830 was a national phase of International Application No. PCT/US2005/017339, filed May 16, 2005. International Application No. PCT/US2005/017339 claimed the benefit of U.S. Provisional Application No. 60/571,090, filed May 14, 2004, and U.S. Provisional Application No. 60/571,092, filed May 14, 2004. International Application No. PCT/US2005/017339 was published in English on Dec. 15, 2005 as WO 2005/117854. These applications are hereby incorporated by reference in their entirety.

FIELD OF THE INVENTION

The present invention relates to aryl ketone compounds for delivering active agents to a target. These compounds are well suited for forming non-covalent mixtures with active agents for oral and other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, epithelium, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many active agents would be the route of choice for administration to animals if not for biological, chemical, and physical barriers. Among the numerous agents which are not typically amenable to oral administration are biologically or chemically active peptides, such as calcitonin and insulin; polysaccharides, such as mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536, and International Patent Publication Nos. WO 98/49135; WO 00/06534; WO 00/07979; WO 00/40203; WO 00/47188; WO 00/50386; WO 00/59863; WO 01/32130, WO 01/32596, WO 01/44199, WO 01/51454, WO 02/02509, WO 02/15959, WO 02/16309, WO 02/20466, WO 02/19969, WO 02/69937, and WO 03/45306.

More recently, a polymer has been conjugated to a modified amino acid or a derivative thereof via a linkage group to provide for polymeric delivery agents. See International Patent Publication No. WO 00/40203.

However, there is still a need for simple, inexpensive delivery systems which are easily prepared and which can deliver active agents by various routes.

SUMMARY OF THE INVENTION

The present invention provides aryl ketone compounds and compositions containing them which facilitate the delivery of active agents. The aryl ketone compounds have the formula

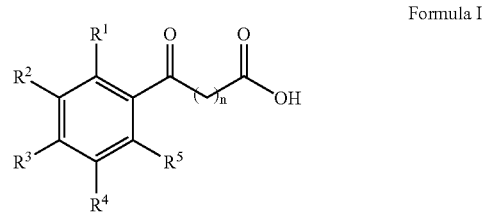

Formula I or a salt thereof, where
n=1 to 9, and
$R^1$ to $R^5$ are independently hydrogen, $C_1$ to $C_6$ alkyl, $C_1$ to $C_6$ alkoxy, $C_2$ to $C_6$ alkenyl, halogen, hydroxyl, —NH—C(O)—$CH_3$, or —O—$C_6H_5$. Preferably, $R^1$ to $R^5$ are independently hydrogen, $C_1$ to $C_4$ alkyl, $C_1$ to $C_4$ alkoxy, $C_2$ to $C_4$ alkenyl, halogen, or hydroxyl.

In one preferred embodiment, n=2-8.
In another preferred embodiment, n=8.
In another preferred embodiment, n=7.
In another preferred embodiment, n=6.
In another preferred embodiment, n=5.
In another preferred embodiment, n=4.
In another preferred embodiment, n=3.
In another preferred embodiment, n=2 and $R^1$ to $R^5$ are hydrogen.
In another preferred embodiment, n=8 and $R^1$ to $R^5$ are hydrogen.
In another preferred embodiment, n=7 and $R^1$ to $R^5$ are hydrogen.

In another preferred embodiment, n=6 and $R^1$ to $R^5$ are hydrogen.

In another preferred embodiment, n=5 and $R^1$ to $R^5$ are hydrogen.

In another preferred embodiment, n=4 and $R^1$ to $R^5$ are hydrogen.

In another preferred embodiment, n=3 and $R^1$ to $R^5$ are hydrogen.

In another preferred embodiment, $R^1$ and $R^5$ are hydrogen.

In another preferred embodiment, $R^1$ and $R^5$ are hydrogen and n=2

In another preferred embodiment, $R^3$ is a hydroxyl.

In another preferred embodiment, $R^3$ is a hydroxyl and n=8.

In another preferred embodiment, $R^1$ is a hydroxyl.

In another preferred embodiment, $R^1$ is a hydroxyl and n=8.

In another preferred embodiment, $R^3$ is methoxy.

In another preferred embodiment, $R^3$ is methoxy and n=2.

In another preferred embodiment, $R^3$ is methoxy and n=3.

In another preferred embodiment, $R^2$ and $R^4$ are independently halogen, and n=2.

In another preferred embodiment $R^2$ and $R^4$ and are flourine.

In another preferred embodiment $R^2$ and $R^4$ are flourine and n=2.

In another preferred embodiment, $R^1$ and $R^3$ are methyl.

In another preferred embodiment, $R^1$ and $R^3$ are methyl and n=2.

In another preferred embodiment, $R^2$ and $R^4$ are methyl, $R^3$ is a methoxy and n=4.

In another preferred embodiment, $R^3$ is an isopropyl.

In another preferred embodiment, $R^3$ is an isopropyl and n=3.

In another preferred embodiment, $R^1$ is methoxy.

In another preferred embodiment, $R^1$ is methoxy and n=2.

In another preferred embodiment, $R^3$ is a halogen.

In another preferred embodiment, $R^3$ is a halogen and n=2.

In another preferred embodiment, $R^3$ is fluorine and n=2.

In another preferred embodiment, $R^3$ is methoxy.

In another preferred embodiment, $R^3$ is a methoxy and n=4.

In another preferred embodiment, $R^2$ and $R^4$ are methyl.

In another preferred embodiment, $R^2$ and $R^4$ are methyl and n=2.

In another preferred embodiment, $R^2$ and $R^4$ are methyl and n=4.

In another preferred embodiment, $R^2$ and $R^4$ are methyl and n=6.

In another preferred embodiment, $R^2$ and $R^3$ are methyl and n=4.

In another preferred embodiment, $R^2$ and $R^3$ are methyl and n=2.

In another preferred embodiment, $R^1$ and $R^4$ are methyl and n=2.

In another preferred embodiment, $R^1$ and $R^4$ are independently halogen.

In another preferred embodiment, $R^1$ and $R^4$ are independently halogen and n=2.

In another preferred embodiment, $R^1$ and $R^4$ are independently halogen and n=4.

In another preferred embodiment, $R^1$ and $R^4$ are chlorine.

In another preferred embodiment, $R^1$ and $R^4$ are chlorine and n=2.

In another preferred embodiment, $R^1$ and $R^4$ are chlorine and n=4.

In another preferred embodiment, $R^1$ and $R^4$ are hydroxyl.

In another preferred embodiment, $R^1$ and $R^4$ are hydroxyl and n=8.

In another preferred embodiment, $R^1$ and $R^4$ are fluorine. More preferably, $R^2$, $R^3$, and $R^5$ are hydrogen.

In another preferred embodiment, $R^1$ and $R^3$ are fluorine. More preferably, $R^2$, $R^4$, and $R^5$ are hydrogen.

In another preferred embodiment, $R^3$ is ethyl. More preferably, $R^1$, $R^2$, $R^4$, and $R^5$ are hydrogen.

In another preferred embodiment, $R^3$ is $C_{1-6}$ alkoxy, such as butoxy or hexyloxy. More preferably, $R^1$, $R^2$, $R^4$, and $R^5$ are hydrogen.

In another preferred embodiment, $R^3$ is $C_{1-6}$ alkyl, such as methyl, propyl, or pentyl. More preferably, $R^1$, $R^2$, $R^4$, and $R^5$ are hydrogen.

In another preferred embodiment, $R^3$ is halogen, such as chlorine. More preferably, $R^1$, $R^2$, $R^4$, and $R^5$ are hydrogen.

In another preferred embodiment, $R^3$ is phenoxy (—O—$C_6H_5$). More preferably, $R^1$, $R^2$, $R^4$, and $R^5$ are hydrogen.

The present invention also includes any combination of the aforementioned R groups and definitions of n.

Preferred compounds include, but are not limited to, the compounds shown below and salts thereof.

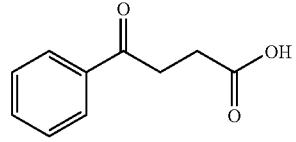

Compound 1

4-Oxo-4-phenyl-butyric acid

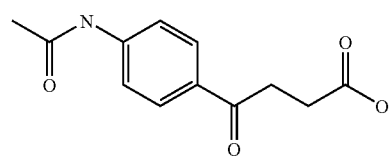

Compound 2

Beta-(4-Acetaminobenzoyl)propionic Acid

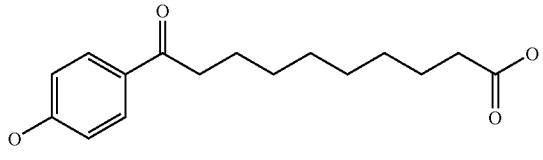

Compound 3

10-(4-hydroxyphenyl)-10-oxodecanoic acid

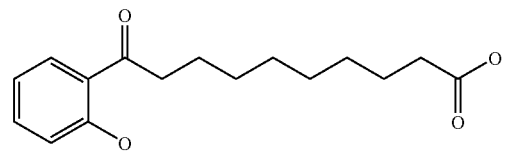

Compound 4

10-(2-Hydroxy-phenyl)-10-oxo-decanoic acid

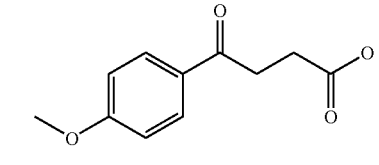

Compound 5

4-(4-Methoxy-phenyl)-4-oxo-butyric acid

Compound 6
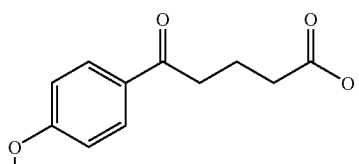
5-(4-Methoxy-phenyl)-5-oxo-pentanoic acid

Compound 7
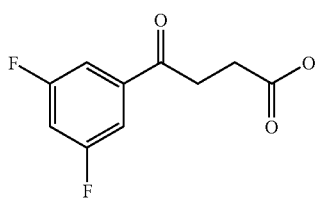
4-(3,5-Difluoro-phenyl)-4-oxo-butyric acid

Compound 8
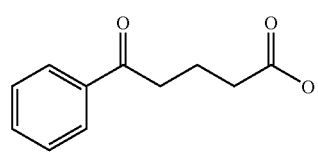
5-Oxo-5-phenyl-pentanoic acid

Compound 9
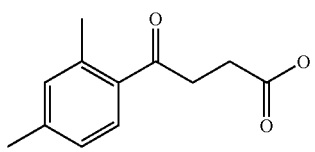
4-(2,4-Dimethyl-phenyl)-4-oxo-butyric acid

Compound 10
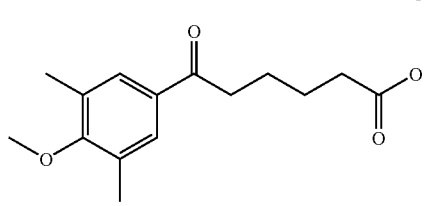
6-(4-Methoxy-3,5-dimethyl-phenyl)-6-oxo-hexanoic acid

Compound 11
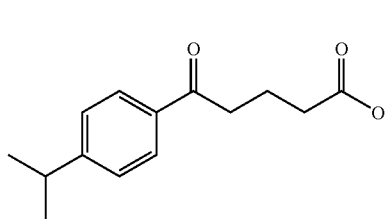
5-(4-Isopropyl-phenyl)-5-oxo-pentanoic acid

Compound 12
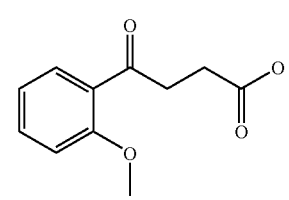
4-(2-Methoxy-phenyl)-4-oxo-butyric acid

Compound 13
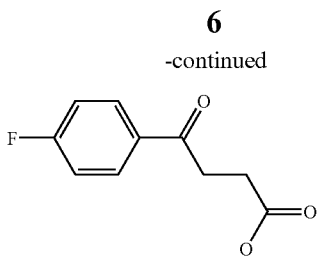
4-(4-Fluoro-phenyl)-4-oxo-butyric acid

Compound 14
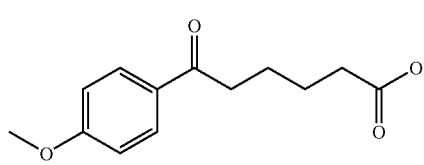
6-(4-Methoxy-phenyl)-6-oxo-hexanoic acid

Compound 15
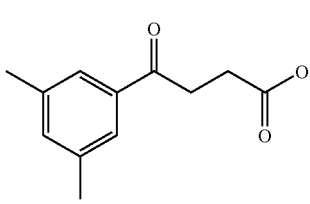
4-(3,5-Dimethyl-phenyl)-4-oxo-butyric acid

Compound 16
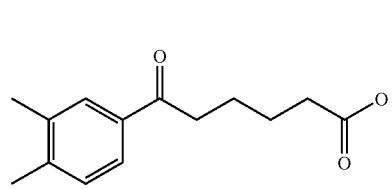
6-(3,4-Dimethyl-phenyl)-6-oxo-hexanoic acid

Compound 17
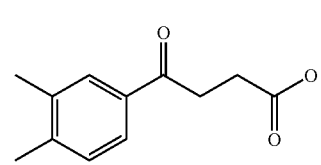
4-(3,4-Dimethyl-phenyl)-4-oxo-butyric acid

Compound 18
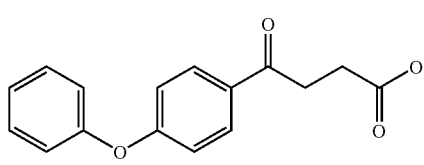
4-Oxo-4-(4-phenoxy-phenyl)-butyric acid

Compound 19
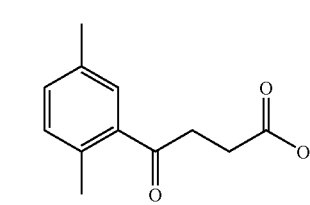
4-(2,5-Dimethyl-phenyl)-4-oxo-butyric acid

-continued

Compound 20

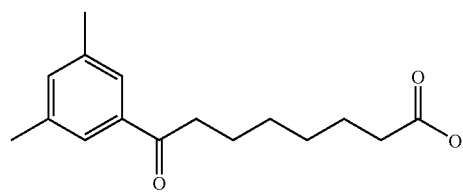

8-(3,5-Dimethyl-phenyl)-8-oxo-octanoic acid

Compound 21

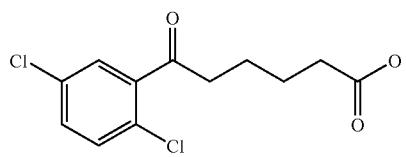

6-(2,5-Dichloro-phenyl)-6-oxo-hexanoic acid

Compound 22

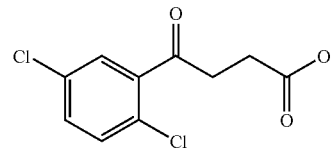

4-(2,5-Dichloro-phenyl)-4-oxo-butyric acid

Compound 23

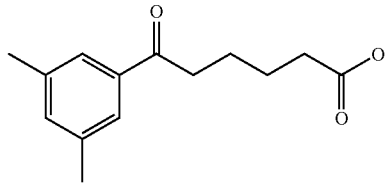

6-(3,5-Dimethyl-phenyl)-6-oxo-hexanoic acid

Compound 24

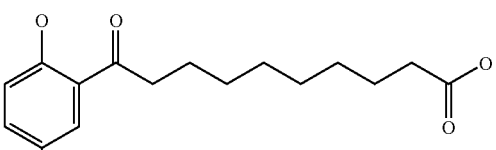

10-(2,5-Dihydroxy-phenyl)-10-oxo-decanoic acid

Compound 25

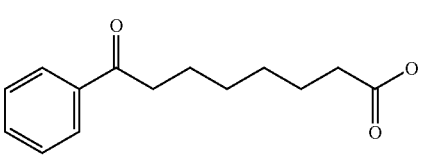

8-Oxo-8-phenyl-octanoic acid

Compound 26

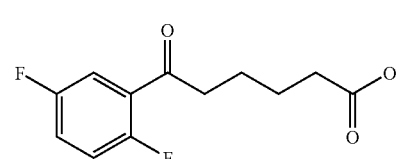

6-(2,5-Difluoro-phenyl)-6-oxo-hexanoic acid

-continued

Compound 27

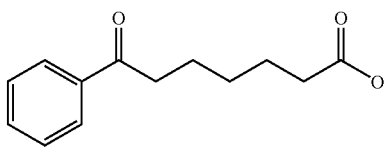

7-Oxo-7-phenyl-heptanoic acid

Compound 28

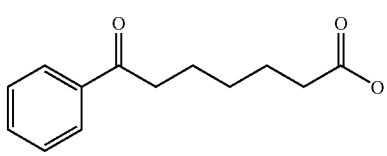

7-Oxo-7-phenyl-heptanoic acid

Compound 29

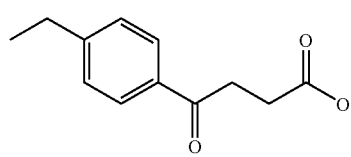

4-(4-Ethyl-phenyl)-4-oxo-butyric acid

Compound 30

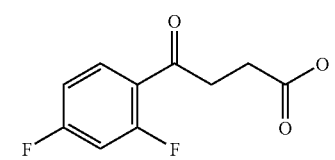

4-(2,4-Difluoro-phenyl)-4-oxo-butyric acid

Compound 31

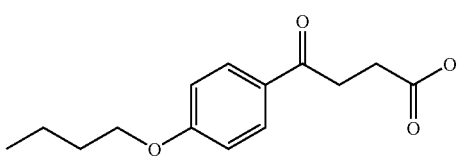

4-(4-Butoxy-phenyl)-4-oxo-butyric acid

Compound 32

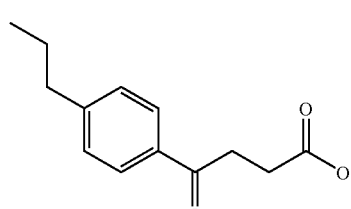

4-Oxo-4-(4-propyl-phenyl)-butyric acid

Compound 33

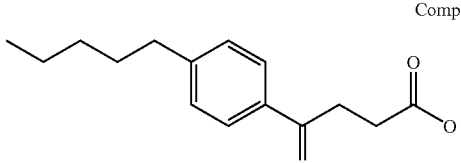

4-Oxo-4-(4-pentyl-phenyl)-butyric acid

-continued

Compound 34

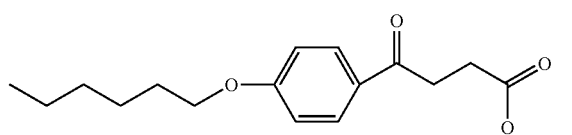

4-(4-Hexyloxy-phenyl)-4-oxo-butyric acid

Compound 35

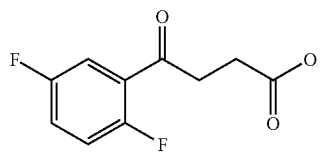

4-(2,5-Difluoro-phenyl)-4-oxo-butyric acid

Compound 36

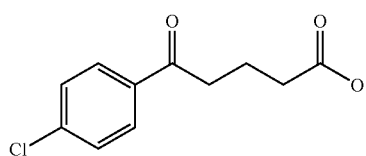

5-(4-Chloro-phenyl)-5-oxo-pentanoic acid

Compound 37

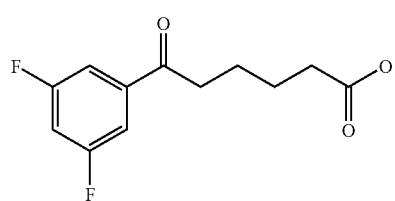

6-(3,5-Difluoro-phenyl)-6-oxo-hexanoic acid

Compound 38

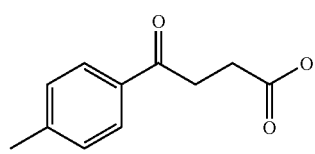

4-Oxo-4-p-tolyl-butyric acid

Compound 39

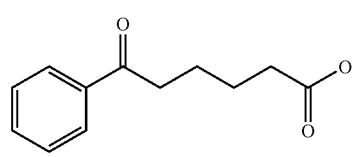

6-Oxo-6-phenyl-hexanoic acid

Compound 40

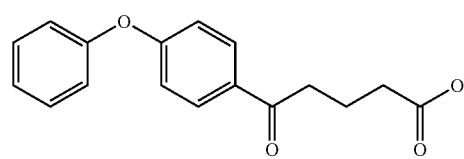

5-Oxo-5-(4-phenoxy-phenyl)-pentanoic acid

-continued

Compound 41

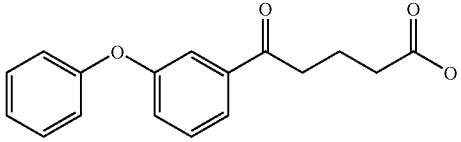

5-Oxo-5-(3-phenoxy-phenyl)-pentanoic acid

Compound 42

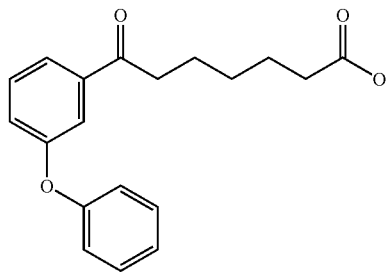

7-Oxo-7-(3-phenoxy-phenyl)-heptanoic acid

Mixtures of these delivery agent compounds may also be used.

The invention also provides a composition (e.g., a pharmaceutical composition) comprising at least one of the delivery agent compounds of the present invention, and at least one active agent. These compositions deliver active agents to selected biological systems in increased or improved bioavailability of the active agent compared to administration of the active agent without the delivery agent compound. Suitable active agents include, but are not limited to, mucopolysaccharides and polypeptides. Preferred active agents include, but are not limited to, heparin, calcitonin, parathyroid hormone (including its fragments, such as pTH[1-34]), insulin, and PYY[3-36]. A more preferred active agent is insulin.

According to one embodiment, the active agent is heparin (e.g., unfractionated heparin or low molecular weight heparin).

According to another embodiment, the active agent is calcitonin.

According to yet another embodiment, the active agent is parathyroid hormone or a fragment thereof (such as pTH[1-34]).

According to yet another embodiment, the active agent is PYY or a PYY agonist (e.g., PYY[3-36]).

According to yet another embodiment, the active agent is insulin.

Also provided is a dosage unit form comprising the composition of the present invention. The dosage unit form may be in the form of a liquid or a solid, such as a tablet, capsule or particle, including a powder or sachet.

Another embodiment is a method for administering an active agent to an animal (e.g., a mammal such as a human), by administering a composition comprising at least one of the delivery agent compounds of the present invention and the active agent to the animal. Routes of administration include the oral, intracolonic and pulmonary routes.

Yet another embodiment is a method of treating a disease or for achieving a desired physiological effect in an animal (e.g., a mammal such as a human) by administering the composition or dosage unit form of the present invention. Typically, the animal is in need of such treatment.

Yet another embodiment is a method of preparing a composition or dosage unit form of the present invention by mixing at least one delivery agent compound of the present invention, and at least one active agent.

DETAILED DESCRIPTION OF THE INVENTION

Delivery Agent Compounds

The terms "alkyl", "alkoxy", "alkenyl", and "alkynyl" as used herein include linear and branched alkyl, alkoxy, alkenyl, and alkynyl substituents, respectively.

The term "$C_1$-$C_6$ alkyl" includes, but is not limited to, methyl, ethyl, propyl, isopropyl, butyl, t-butyl, pentyl, and hexyl.

The term "$C_1$-$C_6$ alkoxy" includes, but is not limited to, methoxy, ethoxy, propoxy, butoxy, pentyloxy, and hexyloxy.

The delivery agent compounds of the present invention may be prepared by the same method with the appropriate starting materials as that used to prepare compound 1 in the examples below.

The delivery agent compounds may be in the form of the carboxylic acid or salts thereof (e.g., pharmaceutically acceptable salts thereof). Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates and hydrates.

Salts of the delivery agent compounds of the present invention may be prepared by methods known in the art. For example, sodium salts may be prepared by dissolving the delivery agent compound in ethanol and adding aqueous sodium hydroxide.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, acetone, methanol, and tetrahydrofuran (THF) and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent may contain a polymer conjugated to it by a linkage group selected from the group consisting of —NHC(O)NH—, —C(O)NH—, —NHC(O), —OOC—, —COO—, —NHC(O)O—, —OC(O)NH—, —$CH_2$NH —NHCH$_2$—, —$CH_2$NHC(O)O—, —OC(O)NHCH$_2$—, —$CH_2$NHCOCH$_2$O—, —OCH$_2$C(O)NHCH$_2$—, —NHC (O)CH$_2$O—, —OCH$_2$C(O)NH—, —NH—, —O—, and carbon-carbon bond. According to one embodiment, the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene, polyacrylates, polymethacrylates, poly(oxyethylene), poly(propylene), polypropylene glycol, polyethylene glycol (PEG), and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract including by acid hydrolysis, enzymes and the like. Also included as suitable active agents are those macromolecular agents whose physiochemical characteristics, including, size, structure or charge, prohibit or impede absorption when dosed orally.

For example, an agent that is to enter the body, or that can benefit from improved pharmacokinetics including delivery, for example when oral bioavailability is limited or nonexistent. These agents are biologically or chemically active agents suitable for use in the present invention include, but are not limited to, macromolecules, such as peptides, including proteins and polypeptides, including dipeptides; hormones; and saccharides, including monosaccharides, polysaccharides, including disaccharides, mixtures of mucopolysaccharides; carbohydrates; lipids; and small polar organic molecules (i.e. polar organic molecules having a molecular weight of 500 daltons or less); nucleosides, other organic compounds; and particularly compounds without oral bioavailability or with limited oral bioavailability, including those compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof:

| Active Agent |
| --- |
| Adrenocorticotropin |
| Amylin and Amylin Agonists |
| Antigens |
| Antimicrobials, including Antibiotics, Anti-Bacterials and Anti-Fungal Agents; non-limiting examples of Antibiotics include Gram-Positive Acting, Bacteriocidal, Lipopeptidal and Cyclic Peptidal Antibiotics, such as Daptomycin And Analogs thereof |
| Anti-Migraine Agents such as BIBM-4096BS BIBN4096BS - (1-Piperidinecarboxamide•N-[2-[[5-amino-1-[[4-(4-pyridinyl)-1-piperazinyl]carbonyl]pentyl]amino]-1-[(3,5-dibromo-4-hydroxyphenyl)methyl]-2-oxoethyl]-4(1,4-dihydro-2-oxo-3(2H0-quinazolinyl)-•[R—(R*,S*)]—) And Other Calcitonin Gene-Related Proteins Antagonists, Sumatriptan Succinate |
| Antivirals including Acyclovir, Valacyclovir |
| Atrial naturetic factor |

| Active Agent |
| --- |
| Bisphosphonates including Alendronate, Clodronate, Etidronate, Ibandronate, Incadronate, Minodronate, Neridronate, Olpadronate, Pamidronate, Risedronate, Tiludronate, Zoledronate, EB1053, and YH529 |
| Calcitonin including Salmon, Eel, Porcine And Human Calcitonin |
| Cholecystokinin (CCK) And CCK Agonists Including CCK-8 |
| CPHPC |
| Cromolyn sodium (Sodium Or Disodium Chromoglycate) |
| Cyclosporin |
| Desferrioxamine (DFO) |
| dipeptidyl peptidase IV (DPP-4) inhibitors |
| Erythropoietin |
| Exedin and Exedin Agonists, including Exendin-3 and Exendin-4 |
| Filgrastim (Granulocyte Colony Stimulating Factor); GM-CSF, (sargramostim) |
| Gallium nitrate |
| Follicle Stimulating Hormone (recombinant and natural) |
| Glucagon |
| Glucagon-Like Peptide 1 (GLP-1), Glucagon, and Glucagon-Like Peptide 2 (GLP-2) |
| Glucocerebrosidase |
| Gonadotropin releasing hormone |
| Growth Hormone Releasing Factor; |
| Growth Hormone Releasing Hormones; |
| Growth Hormones, Including Human Growth Hormones (hGH), Recombinant Human Growth Hormones (rhGH), Bovine Growth Hormones, And Porcine Growth Hormones; |
| Heparin, including Unfractionated Heparin, Heparinoids, Dermatans, Chondroitins, Low Molecular Weight Heparin, Very Low Molecular Weight Heparin Ultra Low Molecular Weight Heparin and synthetic heparins including Fondiparinux; |
| Insulin (including porcine, bovine, human, and human recombinant, optionally having counter ions including zinc, sodium, calcium and ammonium); Insulin-like growth factor IGF-1 |
| interferons, including α (e.g., interferon alfacon-1 (available as Infergen ® from Intermune, Inc. of Brisbane, Ca)), β, omega and γ |
| Interleukins (e.g. Interleukin-1; interleukin-2, interleukin-11, and interleukin-21) |
| Leptin (OB Protein) |
| Leutinizing hormone; leutinizing-hormone-releasing-hormone; follicle stimulating hormone |
| Monoclonal antibodies (including Retuxin and TNF-alpha soluble receptors) |
| Oxytocin |
| Parathyroid hormone (PTH), including its fragments (including PTH 1-34 and PTH 1-38) |
| Peptide YY (PYY), a PYY agonist, or a mixture thereof (including PYY[3-36]) |
| Prostaglandins |
| Protease inhibitors |
| Somatostatin/octreotide |
| Thrombopoietin |
| Vaccines Including Those Against Anthrax or *Y. Pestis*, Influenza, and Herpes |
| Vancomycin |
| Vasopressin |
| Vitamins | including secretagogues, analogs, fragments, mimetics or polyethylene glycol (PEG)-modified derivatives of these compounds; or any combination thereof.

By "peptide YY" or "PYY" is meant a Peptide YY polypeptide obtained or derived from any species. Thus, the term "PYY" includes both the human full length, 36 amino acid peptide as set forth in SEQ ID NO: 2 of International Publication No. WO 02/47712 (which is the PCT counterpart to U.S. Patent Publication No. 2002/0141985, which is hereby incorporated by reference) and Tatemoto, *Proc Natl Acad Sci U.S.A.* 79:2514-8, 1982, and species variations of PYY, including e.g., murine, hamster, chicken, bovine, rat, and dog PYY, for example. By "PYY agonist" is meant any compound which elicits an effect of PYY to reduce nutrient availability, for example a compound (1) having activity in the food intake, gastric emptying, pancreatic secretion, or weight loss assays described in Examples 1, 2, 5, or 6 of WO 02/47712 and U.S. Patent Publication No. 2002/0141985, and (2) which binds specifically in a Y receptor assay (Example 10 of WO 02/47712 and U.S. Patent Publication No. 2002/0141985) or in a competitive binding assay with labeled PYY or PYY [3-36] from certain tissues having an abundance of Y receptors, including e.g., area postrema (Example 9 of WO 02/47712 and U.S. Patent Publication No. 2002/0141985), wherein the PYY agonist is not pancreatic polypeptide. Preferably, PYY agonists would bind in such assays with an affinity of greater than about 1 µM, and more preferably with an affinity of greater than about 1 to about 5 nM.

Such agonists can comprise a polypeptide having a functional PYY domain, an active fragment of PYY, or a chemical or small molecule. PYY agonists may be peptide or nonpeptide compounds, and include "PYY agonist analogs," which refer to any compound structurally similar to a PYY that have PYY activity typically by virtue of binding to or otherwise directly or indirectly interacting with a PYY receptor or other receptor or receptors with which PYY itself may interact to elicit a biological response. Such compounds include derivatives of PYY, fragments of PYY, extended PYY molecules having more than 36 amino acids, truncated PYY molecules having less than 36 amino acids, and substituted PYY molecules having one or more different amino acids, or any combination of the above. Such compounds may also be modified by processes such as pegylation, amidation, glycosylation, acylation, sulfation, phosphorylation, acetylation and cyclization.

One such PYY agonist analog is PYY [3-36], identified as SEQ ID NO: 3 of WO 02/47712 and U.S. Patent Publication No. 2002/0141985; Eberlein, Eysselein et al., *Peptides* 10:797-803 (1989); and Grandy, Schimiczek et al., *Regul*

*Pept* 51:151-9 (1994). Polypeptides with numbers in brackets refer to truncated polypeptides having the sequence of the full length peptide over the amino acid positions in the brackets. Thus, PYY [3-36] has a sequence identical to PYY over amino acids 3 to 36. PYY[3-36] contains approximately 40% of total peptide YY-like immunoreactivity in human and canine intestinal extracts and about 36% of total plasma peptide YY immunoreactivity in a fasting state to slightly over 50% following a meal. It is apparently a dipeptidyl peptidase-IV (DPP4) cleavage product of peptide YY. Peptide YY[3-36] is reportedly a selective ligand at the Y2 and Y5 receptors, which appear pharmacologically unique in preferring N-terminally truncated (i.e. C terminal fragments of) neuropeptide Y analogs. A PYY agonist may bind to a PYY receptor with higher or lower affinity, demonstrate a longer or shorter half-life in vivo or in vitro, or be more or less effective than native PYY.

Other suitable PYY agonists include those described in International Publication No. WO 98/20885, which is hereby incorporated by reference.

The term "heparin" as used herein refers to all forms of heparin, including, but not limited to, unfractionated heparin, heparinoids, dermatans, chondroitins, low molecular weight heparin (e.g., tinzaparin (including tinzaparin sodium)), very low molecular weight heparin, and ultra low molecular weight heparin. Non-limiting examples include unfractionated heparin, such as heparin sodium (e.g., heparin sodium USP, available from Scientific Protein Labs of Waunakee, Wis.). Heparin generally has a molecular weight of from about 1,000 or 5,000 to about 30,000 Daltons. The term "low molecular weight heparin" generally refers to heparin in which at least about 80% (by weight) of the heparin and has a molecular weight of between about 3000 and about 9000 daltons. Non-limiting examples of low molecular weight heparin include tinzaparin, enoxaprin, and daltiparin. Tinzaparin has been approved by the U.S. Food & Drug Administration for the treatment of acute symptomatic deep vein thrombosis with or without pulmonary embolism when administered in conjunction with warfarin sodium. The sodium salt of tinazaparin is available under the trademark Innohep® from Pharmion Corporation of Boulder, Colo. The term "very low molecular weight heparin" generally refers to heparin in which at least about 80% (by weight) of the heparin has a molecular weight of between about 1500 and about 5000 daltons. A non-limiting example of very low molecular weight heparin is bemiparin. The term "ultra low molecular weight heparin" generally refers to heparin in which at least about 80% (by weight) of the heparin has a molecular weight of between about 1000 and about 2000 daltons. A non-limiting examples of ultra low molecular weight heparin is fondiparinux.

The term "insulin" refers to all forms of insulin, including, but not limited to, naturally derived insulin and synthetic forms of insulin, such as those described in U.S. Pat. Nos. 4,421,685, 5,474,978, and 5,534,488, each of which is hereby incorporated by reference in its entirety. According to one embodiment, insulin is administered at a dose of about 0.025 to about 1.0 mg per kilogram of body weight of the recipient per day (mg/kg/day), about 0.06 to about 0.25 mg/kg/day, or about 0.09 to about 0.19 mg/kg/day (based on the weight of active agent). The desired dose may be administered either as a single or divided dose.

Delivery Systems

The composition of the present invention comprises one or more delivery agent compounds of the present invention, and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, or erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent. The amount may be more than a typical amount if the dosage unit form is intended for prolonged dosing such as in a sustained release form.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

Generally, the weight ratio of delivery agent to active agent ranges from about 0.1:1 to about 1000:1 and preferably from about 1:1 to about 300:1. The weight ratio will vary according to the active agent and the particular indication for which the active agent is administered.

The presently disclosed delivery agent compounds enable and/or facilitate the delivery of biologically and chemically active agents, including in oral, intranasal, sublingual, gastric, intestinal, including intraduodenal, jejunal and ileul delivery, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; insects and mammal including, but not limited to: rodents, aquatic mammals, domestic animals such as dogs and cats, farm animals such as sheep, pigs, cows and horses, and primates, preferably humans.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful for orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering the active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Preferably, an effective amount of the composition for the treatment or prevention of the desired disease or for achieving the desired physiological effect is administered. Specific indications for active agents can be found in the Physicians' Desk Reference ($58^{th}$ Ed., 2004, Medical Economics Company, Inc., Montvale, N.J.), which is herein incorporated by reference. The active agents in the table below include their secretagogues, analogs, fragments, mimetics, and polyethylene glycol-modified derivatives.

| Active Agent | Disease and Physiological Effect |
| --- | --- |
| Amylin and Amylin Agonists; | Obesity |
| Adrenocorticotropin; | High Cholesterol (To Lower Cholesterol) |
| Antigens; | Infection |
| Antivirals including Acyclovir, Valacyclovir; | Viral Infections, including Herpes simplex type I and type II |
| Growth hormones (including human recombinant growth hormone and growth-hormone releasing factors and its analogs) | Growth disorders |
| Interferons, including α, β and γ | Viral infection, including chronic cancer, hepatitis, and multiple sclerosis |
| Interleukins (e.g. Interleukin-1; interleukin-2, interleukin-11, and interleukin-21) | Viral infection; cancer; cell mediated immunity; and transplant rejection; |
| Insulin; Insulin-like growth factor IGF-1 | Diabetes |
| Heparin | Treatment and Prevention of Thrombosis, including (Deep Vein Thrombosis); prevention of blood coagulation |
| Calcitonin including Salmon, Eel, Porcine And Human Calcitonin; | Osteoporosis; diseases of the bone; bone pain; analgesic (including pain associated with osteoporosis or cancer) |
| Cholecystokinin (CCK) And CCK Agonists Including CCK-8; | Obesity |
| Erythropoietin | Anemia; HIV/HIV-therapy Associated Anemia; Chemotherapeutically-Induced Anemia |
| Atrial naturetic factor | Vasodilation |
| Antigens | Infection |
| CPHPC | Reduction of amyloid deposits and systemic amyloidoisis often (but not always) in connection with Alzheimer's disease, Type II diabetes, and other amyloid-based diseases |
| Monoclonal antibodies (Antibodies including Retuxin, TNF-alpha soluble receptors;) | To prevent graft rejection; cancer; used in assays to detect diseases |
| Leptin (OB Protein) | Obesity |
| Somatostatin/octreotide | Bleeding ulcer; erosive gastritis; variceal bleeding; diarrhea; acromegaly; TSH-secreting pituitary adenomas; secretory pancreatic tumors; carcinoid syndrome; reduce proptosis/thyroid-associated ophthalmopathy; reduce macular edema/retinopathy |
| Protease inhibitors | HIV Infection/AIDS |
| Adrenocorticotropin | High cholesterol (to lower cholesterol) |
| Gonadotropin releasing hormone | Ovulatory disfunction (to stimulate ovulation) |

-continued

| Active Agent | Disease and Physiological Effect |
| --- | --- |
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim (Granulocyte Colony Stimulating Factor); GM-CSF, (sargramostim) | shorten the duration of chemotherapy-induced neutropenia and thus treat or prevent infection in chemotherapy patients; Inhibit the growth of or to kill Mycobacterium Intracellular Avium Infection (MAC) |
| Prostaglandins | Hypertension |
| Cyclosporin | Transplant rejection |
| Vasopressin | Nocturnal Enuresis; antidiuretic |
| Cromolyn sodium; | Asthma; allergies |
| Vancomycin | Treat or prevent antimicrobial-induced infections including, but not limitted to methacillin-resistant *Staphalococcus aureus* and *Staph. epidermiditis* |
| gallium nitrate | Osteoporosis; Paget's disease; Inhibits osteoclasts; Promotes osteoblastic activity, hypercalcemia, including cancer related hypercalcemia, urethral (urinary tract) malignancies; anti-tumors, cancers, including urethral and bladder cancers; lymphoma; malignancies (including bladder cancer); leukemia; management of bone metastases (and associated pain); muliple myeloma, attenuate immune response, including allogenic transplant rejections; disrupt iron metabolism; promote cell migration; wound repair; to attenuate or treat infectious processes of *mycobacterium* species, including but not limited to *mycobacterium tubercolosis*, and *mycobacterium avium* complex |
| Desferrioxamine (DFO) | Iron overload |
| Parathyroid hormone (PTH), including its fragments. | Osteoporosis; Diseases of the bone |
| Antimicrobials | Infection including but not limited to gram-positive bacterial infection |
| Vitamins | Treat and prevent Vitamin deficiencies |
| Bisphosphonates including Alendronate, Clodronate, Etidronate, Ibandronate, Incadronate, Minodronate, Neridronate, Olpadronate, Pamidronate, Risedronate, Tiludronate, Zoledronate, EB1053, and YH529; | Osteoporosis; Paget's disease; bone tumors and metastases (and associated pain); Breast cancer; including as adjuvant therapy for early stage breast cancer; management of bone metastases (and associated pain), including bone metastases associate with breast cancer, prostate cancer, and lung cancer; Inhibits osteoclasts; Promotes osteoblastic activity; treat and/or prevent bone mineral density (bmd) loss; multiple myeloma; prevention of bone complications related to malignant osteolysis; fibrous dysplasia; pediatric osteogenesis imperfecta; hypercalcemia, urethral (urinary tract) malignancies; reflex sympathetic dystropy synodrome, acute back pain after vertebral crush fracture, chronic inflammatory joint disease, renal bone disease, extrosseous calcifications, analgesic, vitamin D intoxication, periarticular ossifications |
| Anti-Migraine Agents such as BIBM-4096BS BIBN4096BS - (1-Piperidinecarboxamide•N-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-•[R—(R*,S*)]—) And Other Calcitonin Gene-Related Proteins Antagonists, Sumatriptan Succinate; | Anti-migraine; calcitonin gene-related peptide antagonist |
| Glucagon | improving glycemic control (e.g. treating hypoglycemia and controlling hypoglycemic reactions), obesity; a diagnostic aid in the radiogical examination of the stomach, duodenum, small bowel and colon; Treat acute poisoning With Cardiovascular Agents including, but not limited to, calcium channel blockers, beta blockers |

-continued

| Active Agent | Disease and Physiological Effect |
|---|---|
| GLP-1, Exendin - 3, Exendin - 4 | Diabetes; improving glycemic control (e.g. treating hypoglycemia and controlling hypoglycemic reactions), obesity |
| dipeptidyl peptidase IV (DPP-4) inhibitors | Diabetes; improving glycemic control (e.g. treating hypoglycemia), obesity |
| Vaccines Including Those Against Anthrax Or Y. Pestis, Influenza, and Herpes; | Prevent or Minimize Disease or Infection |
| Peptide YY (PYY), PYY agonists, and mixtures thereof | Obesity, Diabetes, Eating Disorders, Insulin-Resistance Syndromes |

For example, one embodiment of the present invention is a method for treating a patient having or susceptible to diabetes by administering insulin and at least one of the delivery agent compounds of the present invention.

Following administration, the active agent present in the composition or dosage unit form is taken up into the circulation. The bioavailability of the agent can be readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

EXAMPLES OF THE PREFERRED EMBODIMENTS

The following examples illustrate the invention without limitation. All parts are given by weight unless otherwise indicated.

Proton nuclear magnetic resonance ($^1$H NMR) analyses for the compounds listed below were conducted on a 300 MHz Bruker® spectrometer (Bruker-Physik AG, Silberstreifen, GERMANY) or a 400 MHz JEOL spectrometer (JEOL USA, Inc., Peabody, Mass.) using dimethyl sulfoxide (DMSO-$d_6$) as the solvent unless otherwise indicated.

Liquid chromatograph/mass spectrometry (LC-MS) analyses were performed with an Agilent Technologies, LC/MSD 1100 (single quad) having the following parameters:

Mobile Phase A: 50:950:5 acetonitrile:water:acetic acid (v/v/v)

Mobile Phase B: 950:50:5 acetonitrile:water:acetic acid (v/v/v)

Gradient Elution: 4 minute linear gradient 0-100% B; total time per injection is 11 minutes Injection volume: 5 uL Column: ZORBAX Rapid Resolution Cartridge, SB-C18, 2.1×30 mm, 3.5 um Particle size, catalog #873700-902

Column temp: 40° C.

UV detection at 244 nm

MSD parameters:

Source: API-ES, positive polarity

Scan Parameters:

| Mass Range: | 125.00-600.00 |
|---|---|
| Fragmentor: | 60 V |
| Gain: | 1.0 EMV |
| Threshold: | 150 |

Spray Chamber:

| Gas Temp. | 350 deg. D |
|---|---|
| Drying Gas: | 12.0 l/min |
| Neb. Pressure; | 40 psig |
| VCap | 4000 V positive/negative |

Example 1

Preparation of Compounds

Compounds can be prepared according to the reactions for the preparation of compound 1 with the appropriate starting materials (Compound 1) 4-Oxo-4-phenyl-butyric acid To 10 g (56 mmol) of 3-benzoylpropionic acid (purchased such as Aldrich Corp. (St. Louis, Mo.), catalog no. B13802) was added 10 mL water. The mixture was stirred and 28 mL of 2N sodium hydroxide (aqueous) was added. The resulting solution was stirred for 2 hours and the solid product was collected after the solution was by lyophilized. 1H NMR (d6-DMSO): δ 7.9, d, 2H, (arylH's); δ 7.6, t, 1H, (arylH's); δ 7.5, t, 2H, (arylH's); δ 3.1, t, 2H (CH$_2$ α to carbonyl); δ 2.2, t, 2H (CH$_2$ α to COOH); COOH peak not observed due to water present in sample.

Compound 1 was also purchased from Aldrich, catalog number B13802.

(Compound 2)
4-(4-Acetylamino-phenyl)-4-oxo-butyric acid

To a 500 mL flask, equipped with mechanical stirrer and under inert atmosphere, was added acetanilide (50 g, 370 mmol), succinic anhydride (37 g, 370 mmol), and 200 mL carbon disulfide. The reaction vessel was cooled with an external ice bath while aluminum (III) trichloride (185 g, 1390 mmol) was added over 1 hour. Additional carbon disulfide (75 mL) was added, the reaction stirred for 1 hour with external ice bath, and then stirred at room temperature for 18 hours. The reaction vessel was cooled with an external ice bath and ice (75 mL) was added to the reaction to quench. The mixture was transferred to a 2 L beaker and ice was added until the final volume was 1400 mL. The insoluble material was collected by suction filtration and washed with 2×100 mL of water. The solid was then dissolved in 1000 mL of 8% aqueous sodium bicarbonate and stirred for 3 hours, diluted with an additional 200 mL of water, and filtered to remove insoluble impurities. The filtered solution was acidified with 1 M aqueous hydrochloric acid until pH=2. The crude product precipitate was collected by filtration and was re dissolved in hot (80-85° C.) water (1250 mL), insoluble material removed by decanting and the mixture cooled to 4° C. The product (8.45 g, 10%) was isolated by filtration as yellow off-white crystals. Found: C, 61.20, H, 5.63%, N, 5.94%; $C_{12}H_{23}NO_4$ requires C, 61.27; H, 5.58%, N, 5.96%; 1H NMR (d6-DMSO): δ 12.2, s, 1H (COOH); δ 10.3, s, 1H(NH); δ 7.9, d, 2H (aryl H's); δ 7.7 d, 2H (aryl H's); 3.2, t, 2H(CH$_2$ α to carbonyl); δ 2.6, t, 2H(CH$_2$ α to COOH); δ 2.1, s, 3H(CH$_3$).

(Compound 3)
10-(4-Hydroxy-phenyl)-10-oxo-decanoic acid

A 500 mL flask, equipped with a reflux condenser and under inert atmosphere, was charged with decanedioic acid (20 g, 296 mmol) and acetic anhydride (280 mL, 2.96 mol). The mixture was heated to reflux for 5 hours. Acetic acid and excess acetic anhydride was removed under reduced pressure. The product was used without further purification.

To a 500 mL flask, equipped with mechanical stirrer and under inert atmosphere, was added the previously made Oxacycloundecane-2,11-dione (20 g, 108.5 mmol), phenol (10.22 g, 108.5 mmol), and 200 mL carbon disulfide. Aluminum (III) trichloride (72.34 g, 542 mmol) was added and the reaction stirred for 72 hours. Carbon disulfide was decanted away, and ice was carefully added until most of mixture was dissolved. The insoluble material was collect by suction filtration and washed with 2×100 mL of water. The solid was then dissolved in 100 mL of 1 M aqueous sodium hydroxide and then carefully acidified with 1 M aqueous hydrochloric acid until pH=7.5 The solids that formed were removed by filtration and the parent solution was continued to be acidified until pH 2.5. The crude product precipitate was collected by filtration and was washed with 1×100 mL water. The crude product was dissolved in 100 mL of 1 M aqueous sodium hydroxide and then carefully acidified with 1 M aqueous hydrochloric acid until pH=7.5 and the impurities that precipitated were filtered off. The parent solution was further acidified until pH 2. The crude product was collected by filtration and washed with 2×50 mL water. The product was recrystallized form acetone. The isolated product (1.2 g, 4%) was collected by filtration. Found: C, 69.00; H, 7.81%; $C_{16}H_{22}O_4$ requires C, 69.04; H, 7.97% 1H NMR (d6-DMSO): δ 12.0, bs, 1H(COOH); δ 10.3, bs, 1H (aryl-hydroxyl); δ 7.8 d, 2H (aryl H's); δ 6.8, d, 2H, (aryl H's); δ 2.9, t, 2H(CH$_2$ α to carbonyl); δ 2.2, t, 2H (CH$_2$ α to COOH); δ 1.5, multiplet, 4H(CH$_2$'s β to carbonyl & β to COOH), δ 1.3, multiplet, 8H (rest of CH$_2$'s).

(Compound 4)
10-(2-Hydroxy-phenyl)-10-oxo-decanoic acid

To a 100 mL flask was added methylene chloride (50 mL), 9-bromononanol (7.63 g, 34.2 mmol) and trimethylsilyl chloride (4.5 mL, 35.5 mmol) and allowed to stir under nitrogen for 20 minutes. Triethyl amine (5.0 mL, 35.9 mmol) was then added and the resulting reaction mixture was stirred for 2 hours at room temperature. The reaction mixture was then diluted with 80 mL of hexane, filtered, and then concentrated under reduced pressure. The resulting residue was again diluted with 80 mL of hexane, filtered, and then concentrated under reduced pressure to yield 9.7 g (96%) of a yellow liquid which was used without further purification.

5.69 g (19.3 mmol) of the previously prepared (9-Bromononyloxy)-trimethyl-silane was added drop-wise to a 50 mL flask under an inert atmosphere containing magnesium metal (0.59 g, 24.3 mmol), 20 mL tetrahydrofuran and a small crystal of iodine was used to initiate the Grignard reaction. In a 100 mL flask under inert atmosphere a solution of salicylylaldehyde (2.1 mL, 19.7 mmol) in 20 mL of tetrahydrofuran was cooled with an external ice bath. The cooled aldehyde solution was then treated with 1.0 M lithium bis(trimethylsilyl)amide (20.0 mL, 20 mmol). The Grignard reaction was cooled with an external ice bath after stirring for 1 hour. The cooled Grignard was then added drop-wise via cannula to the aldehyde solution over a 5 minute period with constant stirring. The resulting reaction mixture was allowed to warm to room temperature and continue to stir overnight. The reaction was poured into 40 mL of ethyl acetate and quenched with 15 mL of saturated aqueous sodium bicarbonate solution. The organic layer was separated and washed with 2×25 mL portions of 4% aqueous hydrochloric acid followed by 1×20 mL portion of brine. The organic layer was dried over sodium sulfate, filtered, and the solvent removed under reduced pressure. Residual salicylylaldehyde was removed by Kugelrohr distillation and the resulting residue was used without further purification.

A 100 mL flask was charged with the previously made 1-(2-Hydroxy-phenyl)-undecane-1,11-diol (5.0 g, 18.9 mmol) and 50 mL of dimethyl formamide. To this was added pyridinium dichromate (32.9 g, 87.5 mmol). (The addition was mildly exothermic.) The reaction mixture was stirred at room temperature overnight. The reaction mixture was poured into 50 mL of ethyl acetate and washed with 200 mL of water, 30 mL of 4% aqueous hydrochloric acid, 30 mL water, and finally with 30 mL of brine. The organic layer was then stirred with 10 g of silica gel for 15 minutes, dried with sodium sulfate, filtered, and solvent removed under reduced pressure. The off-white crude product was recrystallized from ethanol/water. The product (0.5 g, 10%) was isolated as an off-white solid, mp 85-87° C. Combustion analysis: Found: C, 69.01; H, 8.36%; $C_{16}H_{22}O_4$ requires C, 69.54; H, 8.02% 1H NMR (d6-DMSO): δ 12.0, s, 1H(COOH); δ 7.9 dd, 1H (aryl H); δ 7.5, dt, 1H, (aryl H); δ 6.9, complex multiplet, 2H (aryl H's), 3.1, t, 2H (CH$_2$ α to carbonyl); δ 2.2, t, 2H (CH$_2$ α to COOH); δ 1.6, multiplet, 2H(CH$_2$ β to carbonyl), δ 1.5, multiplet, 2H(CH$_2$ β to COOH), δ 1.3, multiplet, 8H (rest of CH$_2$'s).

(Compound 5) 4-(4-Methoxy-phenyl)-4-oxo-butyric acid

A 500 mL round bottom flask equipped with a magnetic stirrer bar and an inert atmosphere (nitrogen gas) was charged with 5.25 mL (48.3 mmol) of anisole, 4.83 g (48.3 mmol) of succinic anhydride, 125 mL 1,1,2,2-tetrachloroethane and 125 mL of nitrobenzene. The reaction vessel was cooled with an external ice bath and stirred for 30 minutes. Aluminum trichloride (14.2 g, 106.4 mmol) was added to the pale yellow solution, which then turned to a dark reddish brown color. The ice bath was removed, and the reaction was allowed to stir at room temperature for 36 hours. Reaction was again cooled with an external ice bath. Prepared acidic solution by pouring 1N hydrogen chloride solution into a 100 mL beaker filled with ice. This solution was added to the reaction mixture carefully, drop-wise at first until reaction became clear with white precipitate. After that point a 10 mL portion was carefully added to test for reactivity, and then the remained of the ice/acid mixture was added. A second 100 mL of ice/acid mixture was added, the external ice bath removed and the pale emulsion was stirred for 2 hours. A white precipitate was collected form the emulsion by suction filtration. This solid was dissolved in 300 mL of 0.3 M sodium hydroxide, washed with 100 mL of ethyl acetate, and acidified to ~pH 1 with 1 M hydrochloric acid. The white precipitate that was collected upon vacuum filtration was washed with 3×100 mL de-ionized water and dried. The product (4.7 g, 47%) was isolated as a white solid, mp 149-150° C. Combustion analysis: Found: C, 63.52; H, 5.78%; $C_{11}H_{12}O_4$ requires C, 63.45; H, 5.81% 1H NMR (d6-DMSO): δ 12.2, s, 1H (COOH); δ 7.9 d, 2H (aryl H's); δ 7.0, d, 2H, (arylH's); δ 3.8, s, 3H (OMe H's); δ 3.2, t, 2H(CH$_2$ α to carbonyl); δ 2.5, t, 2H(CH$_2$ α to COOH).

Compound 6)
5-(4-Methoxy-phenyl)-5-oxo-pentanoic acid

This compound was prepared similarly to compound 5, except utilizing glutaric anhydride instead of succinic anhydride, mp 141-142° C. Found: C, 64.65, H, 6.34%; $C_{12}H_{14}O_4$ requires C, 64.85; H, 6.35% 1H NMR (d6-DMSO): δ 12.2, s, 1H(COOH); δ 7.9 d, 2H (aryl H's); δ 7.0, d, 2H, (arylH's); δ 3.8, s, 3H (OMe H's); δ 3.0, t, 2H(CH$_2$ α to carbonyl); δ 2.3, t, 2H(CH$_2$ α to COOH)); δ 1.8 quintuplet, 2H(CH$_2$ between the other two).

Compound 7 was purchased from Aldrich Corp. (St. Louis, Mo.), catalog number 514683.

Compound 8 was purchased from Aldrich, catalog number B12687.

Compound 9 was purchased from Aldrich, catalog number S346810.

Compound 10 was purchased from Rieke Metals, Inc. (Lincoln, Nebr.), catalog number 7013D.

Compound 11 was purchased from Rieke, catalog number 7148C.

Compound 11)
5-(4-Isopropyl-phenyl)-5-oxo-pentanoic acid sodium salt

Compound 11 was prepared as follows. 5-(4-Isopropyl-phenyl)-5-oxo-pentanoic acid (5 g, 21.3 mmol) was dissolved in 75 mL ethanol in a 250 mL flask. Sodium hydroxide (0.85 g, 21.3 mmol) was added and the reaction stirred overnight under reduced pressure on a rotary evaporator. The solid was dried under vacuum and used without further purification. Found: C, 60.24, H, 6.66, Na, 9.21%; $C_{14}H_{17}O_3Na$ requires C, 61.28; H, 6.98, Na, 8.38%. 1H NMR (D2O): δ 7.7, d, 2H (aryl-H's); δ 7.2 d, 2H (aryl H's); δ 2.9, t, 2H(CH$_2$ α to carbonyl); δ 2.8, multiplet, 1H, (CH of isopropyl group); δ 2.1, t, 2H (CH$_2$ α to COOH); δ 1.8, q, 2H (CH$_2$ β to both carbonyl & COOH), δ 1.1, d, 6H (CH$_3$'s of isopropyl group).

Compound 12 was purchased from Rieke, catalog number 7060B.

Compound 13 was purchased from Acros Organics USA (Morris Plains, N.J.), catalog number 17.522.62.

Compound 14 was purchased from Rieke, catalog number 7011D.

Compound 15 was purchased from Rieke, catalog number 7036B.

Compound 16 was purchased from Rieke, catalog number 7012D.

Compound 17 was purchased from Rieke, catalog number 7012B.

Compound 18 was purchased from Rieke, catalog number 7055B.

Compound 19 was purchased from Rieke, catalog number 7005b.

Compound 20 was purchased from Rieke, catalog number 7036F.

Compound 21 was purchased from Rieke, catalog number 7144D.

Compound 22 was purchased from Rieke, catalog number 7144B.

Compound 23 was purchased from Rieke, catalog number 7036D.

(Compound 24)
10-(2,5-Dihydroxy-phenyl)-10-oxo-decanoic acid

A 500 mL flask, equipped with a reflux condenser and under inert atmosphere, was charged with decanedioic acid (20 g, 296 mmol) and acetic anhydride (280 mL, 2.96 mol). The mixture was heated to reflux for 5 hours. Acetic acid and excess acetic anhydride was removed under reduced pressure. The product was used without further purification.

To a 500 mL flask, equipped with mechanical stirrer and under inert atmosphere, was added the previously made Oxacycloundecane-2,11-dione (37.95 g, 206 mmol), 1,4-diacetoxy-benzene (20 g, 103 mmol), and 200 mL carbon disulfide. Aluminum (III) trichloride (68.7 g, 515 mmol) was added and the reaction stirred for 72 hours. Carbon disulfide was decanted away, and ice was carefully added until most of mixture was dissolved. The insoluble material was collected by suction filtration and washed with 2×100 mL of water. The solid was then dissolved in 50 mL of 1 M aqueous sodium hydroxide and stirred for 1 hour. The solution was acidified with 1 M aqueous hydrochloric acid until pH=2. The crude product precipitate was collected by filtration and was re dissolved in acetonitrile (50 mL) and methylene chloride (15 mL) and allowed to precipitate slowly over a week. The resulting brown powder was collected by filtration and recrystallized from 10:3 acetic acid:water. The product (0.8 g, 3%) was isolated by filtration. Found: C, 65.55, H, 7.69%; $C_{16}H_{22}O_5$ requires C, 65.29; H, 7.53% 1H NMR (d6-DMSO): δ 12.0, s, 1H (COOH); δ 11.4, s, 1H (aryl-hydroxyl); δ 9.2, s, 1H (aryl-hydroxyl); δ 7.2 d, 1H (aryl H); δ 7.0, dd, 1H, (arylH); δ 6.8, d, 1H (aryl H's), 3.0, t, 2H(CH$_2$ α to carbonyl); δ 2.2, t, 2H (CH$_2$ β to COOH); δ 1.6, multiplet, 2H (CH$_2$ β to carbonyl), δ 1.5, multiplet, 2H (CH$_2$ β to COOH), δ 1.3, multiplet, 8H (rest of CH$_2$'s).

Compound 25 was purchased from Lancaster Synthesis Inc. (Windham N.H.), catalog number 8395.

Compound 26 was purchased from Rieke, catalog number 7067D.

Compound 27 was purchased from Lancaster, catalog number 8431.

Compound 28 was purchased from Acros, catalog number 34434.

Compound 29 was purchased from Alfa Aesar (Ward Hill, Mass.), catalog number B20767.

Compound 30 was purchased from Rieke, catalog number 7066B.

Compound 31 was purchased from Maybridge Chemicals (Cornwall, England), catalog number BTB10247.

Compound 32 was purchased from Maybridge, catalog number BTB09815.

Compound 33 was purchased from Maybridge, catalog number BTB09813.

Compound 34 was purchased from Maybridge, catalog number BTB10249.

Compound 35 was purchased from Rieke, catalog number 7067B.

Compound 36 was purchased from Acros, catalog number 335595000.

Compound 37 was purchased from Rieke, catalog number 7048D.

Compound 38 was purchased from TCI America (Portland, Oreg.), catalog number M1377.

Compound 39 was purchased from TCI, catalog number B2182.

Compounds 40-42 can be prepared by the aforementioned methods substituting the appropriate starting materials.

Example 2

Experimental Data

Heparin Delivery Oral/Intracolonic Delivery

Oral gavage (PO) and/or intracolonic (IC) dosing solutions containing a delivery agent compound and heparin sodium USP in 25% aqueous propylene glycol were prepared. Either the sodium salt of the compound was used or the free acid was converted to the sodium salt with one equivalent of sodium hydroxide. Typically, delivery agent compound and heparin (about 166-182 IU/mg) were mixed by vortex as dry powders. This dry mixture was dissolved in 25% v/v aqueous propylene glycol, vortexed and placed in a sonicator (about $37^B$ C). The pH was adjusted to about 7 (6.5 to 8.5) with aqueous NaOH (2N). The dosing solution was sonicated to produce a clear solution. The final volume was adjusted to 3.0 mL. The final delivery agent compound dose, heparin dose and volume dose amounts are listed below in Table 2.

The typical dosing and sampling protocols were as follows. Male Sprague-Dawley rats weighing between 275-350 g were fasted for 24 hours and were anesthetized with ketamine hydrochloride (88 mg/kg) intramuscularly immediately prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm 8 fr Rusch catheter was adapted to a 1 ml syringe with a pipette tip. The dosing catheter was inserted into the colon through the anus until the tube was no longer visible. The dosing solution was expressed slowly into the colon.

Citrated blood samples were collected by cardiac puncture following the administration of ketamine (88 mg/kg), typically at time—0.25, 0.5, 1.0 and 1.5 hours. Heparin activity was determined by utilizing the activated partial thromboplastin time (APTT) according to the method of Henry, J. B., Clinical Diagnosis and Management by Laboratory Methods, Philadelphia, Pa., W.B. Saunders (1979). Previous studied indicated baseline values of about 20 sec. Results from the five rats in each group were averaged for each time point. The maximum is reported below in Table 2.

Parathyroid Hormone Delivery (PTH 1-34) Oral/Intracolonic Delivery

Oral gavage (PO) and/or intracolonic (IC) dosing solutions of delivery agent compound and human parathyroid hormone residues 1-34 (PTH) in water were prepared. A solution of the compound was made either with the sodium salt of the compound or by converting the free acid to its sodium salt. Typically, a solution of the compound was prepared in water and stirred, adding one equivalent of sodium hydroxide (1.0 N) when making sodium salt. The final dosing solutions were prepared by mixing the compound with a PTH stock solution (typically having a concentration of 5 mg PTH/ml) and diluting to the desired volume (usually 3.0 ml). The final compound, PTH and volume dose amounts are listed below in Table 4.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm Rusch catheter tube (French 8 or 6) was adapted to a syringe with an Eppendorf pipette tip. The syringe was filled with the dosing solution by drawing the solution through the catheter tube. The catheter tube was wiped dry. K-Y jelly was applied to the tip, avoiding contact with the eye of the tube, and the tube was inserted into the colon through the anus until the tube was no longer visible. The solution was injected by pressing the syringe plunger, and the tube was removed.

Blood samples were collected serially from the tail artery, typically at time=0, 15, 30, 45, 60 and 90 minutes for oral and 0, 10, 20, 30, 60 and 90 for IC dosing. Serum PTH concentrations were quantified by an PTH radioimmunoassay kit (Kit #RIK 6101 from Peninsula Laboratories, Inc. San Carlos, Calif.). Previous studies indicated baseline values of about zero. Results from the five rats in each group were averaged for each time point. The maximum is reported below in Table 4.

TABLE 2

Oral/Intracolonic Delivery of Heparin

| Compound | Method of Administration | volume dose (ml/kg) | Compound Dose (mg/kg) | Heparin Dose (mg/kg) | Mean Peak APTT (sec) ± SD | pH |
|---|---|---|---|---|---|---|
| 4 | IC | 1 | 50 | 25 | 42.90 ± 8.70 | 7.61 |

TABLE 4

Oral/Intracolonic Delivery of PTH in Rats

| Compound | Method of Administration | volume dose (ml/kg) | Compound Dose (mg/kg) | PTH Dose (ug/kg) | Mean Peak Serum [PTH] (pg/ml) ± SD | pH |
|---|---|---|---|---|---|---|
| 3 | Oral | 1 | 100 | 200 | 780.77 ± 439.92 | 8.18 |
| 3 | Oral | 1 | 100 | 200 | 53.51 ± 39.55 | 8.09 |
| 4 | Oral | 1 | 100 | 200 | 135.78 ± 136.97 | 8.41 |

Insulin—Oral Delivery

Oral dosing (PO) compositions of delivery agent compound and human zinc insulin (minimum 26 IU/mg available from Calbiochem—Novabiochem Corp, La Jolla, Calif.) were prepared in deionized water. Typically, 500 mg of delivery agent compound was added to 1.5 ml of water. The free acid of the delivery agent compound was converted to the sodium salt by stirring the resultant solution and adding one equivalent of sodium hydroxide. The solution was vortexed, then heated (about 37° C.) and sonicated. The pH was adjusted to about 7 to 8.5 with NaOH or HCl. Additional NaOH was added, if necessary, to achieve uniform solubility, and the pH re-adjusted to about 7 to 8.5. Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to pH 8.15 and to obtain a clear solution using 40 ml concentrated HCl, 25 ml 10N NaOH and 50 ml 1N NaOH) was added to the solution and mixed by inverting. The final delivery agent compound dose, insulin dose and dose volume amounts are listed.

The typical dosing and sampling protocols were as follows. Male Sprague-Dawley rats weighing between about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=15, 30, 60, 120 and 180 minutes. Serum insulin levels were determined with an Insulin ELISA Test Kit (Kit #DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum human insulin concentrations (μU/ml) were measured for each time point for each of the five animals in each dosing group. The five values for each time point were averaged and the results plotted as serum insulin concentration versus time. (Previous experiments revealed no measurable levels of human insulin following oral dosing with human insulin alone.) The maximum (peak) and the area under the curve (AUC) are reported below in Table 5. For % change from baseline for Blood Glucose the ONE TOUCH® (Life Scan, Johnson & Johnson, New Brunswick, N.J.).

Insulin—Oral Delivery

| Delivery Agent Compound | Delivery Agent Compound Dose (mg/kg) | Insulin Dose (mg/kg) | Volume dose (ml/kg) | % Change in Glucose (from control) |
|---|---|---|---|---|
| 1 | 200 | 0.50 | 1 | −30.7 |
| 5 | 200 | 0.50 | 1 | −12.1 |
| 6 | 200 | 0.50 | 1 | −18.3 |
| 7 | 200 | 0.50 | 1 | −14.4 |
| 7 | 200 | 0.50 | 1 | −37.8 |
| 8 | 200 | 0.50 | 1 | −1.3 |
| 9 | 200 | 0.50 | 1 | −45.1 |
| 9 | 200 | 0.50 | 1 | −8.4 |
| 9 | 200 | 0.50 | 1 | −39.5 |
| 10 | 200 | 0.50 | 1 | −13.5 |
| 12 | 200 | 0.50 | 1 | −2.3 |
| 13 | 200 | 0.50 | 1 | −43.9 |
| 13 | 200 | 0.50 | 1 | −13.7 |
| 14 | 200 | 0.50 | 1 | −2.0 |
| 16 | 200 | 0.50 | 1 | −25.1 |
| 17 | 200 | 0.50 | 1 | −9.5 |
| 19 | 200 | 0.50 | 1 | −28.3 |
| 20 | 200 | 0.50 | 1 | −6.6 |
| 21 | 200 | 0.50 | 1 | −40.8 |
| 22 | 200 | 0.50 | 1 | −16.3 |
| 23 | 200 | 0.50 | 1 | −7.5 |
| 25 | 200 | 0.50 | 1 | −20.8 |
| 26 | 200 | 0.50 | 1 | −50.1 |
| 26 | 200 | 0.50 | 1 | −60.3 |
| 27 | 200 | 0.50 | 1 | −53.0 |
| 27 | 200 | 0.50 | 1 | −54.7 |
| 27 | 200 | 0.50 | 1 | −54.9 |
| 28 | 200 | 0.50 | 1 | −26.4 |
| 29 | 200 | 0.50 | 1 | −35.4 |
| 30 | 200 | 0.50 | 1 | −10.5 |
| 34 | 200 | 0.50 | 1 | 9.4 |
| 35 | 200 | 0.50 | 1 | −11.8 |
| 36 | 200 | 0.50 | 1 | −31.9 |
| 37 | 200 | 0.50 | 1 | −39.0 |
| 38 | 200 | 0.50 | 1 | −26.9 |
| 39 | 200 | 0.50 | 1 | −56.0 |
| 39 | 200 | 0.50 | 1 | −12.5 |
| 40 | 200 | 0.50 | 1 | −3.9 |
| 41 | 200 | 0.50 | 1 | −16.5 |
| 42 | 200 | 0.50 | 1 | −13.8 |

Example

Solid Oral Delivery of PYY[3-36] in Rats

Administration of Solid PYY 3-36 to Feed Restricted Rats.

PYY[3-36] stock solution (80 mg/ml) prepared with deionized water was used.

About 0.08 mg/tablet (about 0.3 mg/kg) of PYY (about 1 μl) was added and blended with either about 13.5 or about 27 mg/tablet (about 50 or 100 mg/kg) Delivery Agent. Upper punch, lower punch and die of Carver 4350 manual pellet press with a Caplet shape model sold by Natoli Engineering Company, Inc. were treated with magnesium stearate (0.1%). About 13.58 or about 27.08 mg of mixed powder was fed into the die and a mini bead shape tablet was made at about 1000 PSI bar pressure. The resulting solid dosage form is about the size of a standard capsule size 9 (about 2.65 mm diameter and about 8.40 mm length) for the 27.08 mg size and about 2.65 mm diameter and about 4.20 mm length for the 13.58 mg solid.

Male Sprague Dawley rats (about 260–about 280 g) were fasted overnight and then anesthesized by standard $CO_2$ inhalation technique for about 10 to 30 seconds resulting in an anesthesized state for about less then one minute, preferably about 10 to about 30 seconds.

An oral dosing tube was used. The dosing tube was inserted into the rat's mouth and carefully threaded down the rats pharynx and esophagus about 8 cm to about 15 cm depending on the weight of the rat (typically about 11 cm). The solid dosage form was delivered into the distal esophagus and/or stomach by pressing the plunger of the oral dosing tube.

Blood samples were collected serially from the tail artery, by cardiac puncture, or as in this case by retro-orbitally, typically at time=0, 15, 30, 60 and 90 minutes. Serum PYY concentrations were quantified using a PYY[3-36] radioimmunoassay (Catalog #RK-059-02 from Phoenix Pharmaceuticals, Inc., Belmont, Calif.). Results from the animals in each group were averaged for each time point. The maximum of these averages (i.e., the mean peak serum PYY[3-36] concentration±standard deviation (SD)) is reported below.

Oral Delivery of PYY[3-36] in Feed Restricted Rats

| Delivery Agent | Method of Administration | Delivery Agent dose (mg/kg) | PYY (3-36) dose (mg/kg) | Mean serum peak of PYY (pg/ml) ± SD |
|---|---|---|---|---|
| 11 - sodium salt form | Oral, solid dose, 1 tablet per animal | 100 | 0.3 | 897.1 ± 257.3 |
| 11 - acid form | Oral, solid dose, 1 tablet per animal | 50 | 0.3 | 161.7 ± 148.5 |

The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A pharmaceutical composition comprising:
(A) at least one biologically active agent selected from human growth hormone, interferon, heparin, low molecular weight heparin, cromolyn sodium, PYY, calcitonin, parathyroid hormone, erythropoietin, and combinations thereof; and
(B) a delivery agent of the formula:

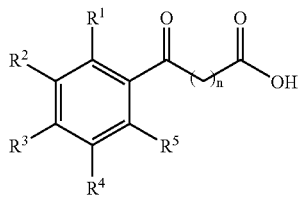

or a salt thereof, wherein
n is an integer from 1 to 9,
$R^2$ to $R^4$ are independently hydrogen, $C_1$ to $C_6$ alkyl, $C_1$ to $C_6$ alkoxy, $C_2$ to $C_6$ alkenyl, halogen, hydroxyl, or —O—$C_6H_5$, and
$R^1$ and $R^5$ are independently hydrogen, $C_1$ to $C_6$ alkoxy, $C_2$ to $C_6$ alkenyl, halogen, or —O—$C_6H_5$,
or a salt thereof.

2. A pharmaceutical composition comprising at least one biologically active agent and a compound selected from:
10-(4-Hydroxy-phenyl)-10-oxodecanoic acid;
5-(4-Methoxy-phenyl)-5-oxo-pentanoic acid;
4-(3,5-Difluoro-phenyl)-4-oxo-butyric acid;
5-Oxo-5-phenyl-pentanoic acid;
5-(4-Isopropyl-phenyl)-5-oxo-pentanoic acid;
4-(2-Methoxy-phenyl)-4-oxo-butyric acid;
4-(4-Fluoro-phenyl)-4-oxo-butyric acid;
6-(4-Methoxy-phenyl)-6-oxo-hexanoic acid;
6-(3,4-Dimethyl-phenyl)-6-oxo-hexanoic acid;
4-(3,4-Dimethyl-phenyl)-4-oxo-butyric acid;
6-(2,5-Dichloro-phenyl)-6-oxo-hexanoic acid;
4-(2,5-Dichloro-phenyl)-4-oxo-butyric acid;
8-Oxo-8-phenyl-octanoic acid;
6-(2,5-Difluoro-phenyl)-6-oxo-hexanoic acid;
7-Oxo-7-phenyl-heptanoic acid;
4-(4-Ethyl-phenyl)-4-oxo-butyric acid;
4-(2,4-Difluoro-phenyl)-4-oxo-butyric acid;
4-(4-Butoxy-phenyl)-4-oxo-butyric acid;
4-Oxo-4-(4-propyl-phenyl)-butyric acid;
4-Oxo-4-(4-pentyl-phenyl)-butyric acid;
4-(4-Hexyloxy-phenyl)-4-oxo-butyric acid;
4-(2,5-Difluoro-phenyl)-4-oxo-butyric acid;
6-(3,5-Difluoro-phenyl)-6-oxo-hexanoic acid;
4-Oxo-4-p-tolyl-butyric acid;
6-Oxo-6-phenyl-hexanoic acid;
5-Oxo-5-(4-phenoxy-phenyl)-pentanoic acid;
5-Oxo-5-(3-phenoxy-phenyl)-pentanoic acid; and
7-Oxo-7-(3-phenoxy-phenyl)-heptanoic acid;
and salts thereof; wherein said biologically active agent is selected from:
Adrenocorticotropin, Amylin, Calcitonin, Sumatriptan Succinate, Calcitonin, Cholecystokinin (CCK), Cromolyn sodium (Sodium Or Disodium Chromoglycate), Desferrioxamine (DFO), Erythropoietin, Exedin, Filgrastim (Granulocyte Colony Stimulating Factor), GM-CSF (sargramostim), Gallium nitrate, Follicle Stimulating Hormone (recombinant and natural), Glucagon, Glucagon-Like Peptide 1 (GLP-1), Glucagon-Like Peptide 2 (GLP-2), Glucocerebrosidase, Gonadotropin releasing hormone, Human Growth Hormone (hGH), Heparin, Unfractionated Heparin, Low Molecular Weight Heparin, Very Low Molecular Weight Heparin, Ultra Low Molecular Weight Heparin, Insulin, Insulin-like growth factor IGF-1, α-interferon, β-interferon, γ-interferon, Leptin (OB Protein), Leutinizing hormone, leutinizing-hormone-releasing-hormone, follicle stimulating hormone, Oxytocin, Parathyroid hormone (PTH), Peptide YY (PYY), Somatostatin/octreotide, Thrombopoietin, Vasopressin, or any combination thereof.

3. A pharmaceutical composition comprising a compound selected from:
10-(4-Hydroxy-phenyl)-10-oxodecanoic acid;
4-(4-Methoxy-phenyl)-4-oxo-butyric acid;
5-(4-Methoxy-phenyl)-5-oxo-pentanoic acid;
4-(3,5-Difluoro-phenyl)-4-oxo-butyric acid;
5-Oxo-5-phenyl-pentanoic acid;
5-(4-Isopropyl-phenyl)-5-oxo-pentanoic acid;
4-(2-Methoxy-phenyl)-4-oxo-butyric acid;
4-(4-Fluoro-phenyl)-4-oxo-butyric acid;
6-(4-Methoxy-phenyl)-6-oxo-hexanoic acid;
6-(3,4-Dimethyl-phenyl)-6-oxo-hexanoic acid;
4-(3,4-Dimethyl-phenyl)-4-oxo-butyric acid;
6-(2,5-Dichloro-phenyl)-6-oxo-hexanoic acid;
4-(2,5-Dichloro-phenyl)-4-oxo-butyric acid;

8-Oxo-8-phenyl-octanoic acid;
6-(2,5-Difluoro-phenyl)-6-oxo-hexanoic acid;
7-Oxo-7-phenyl-heptanoic acid;
4-(4-Ethyl-phenyl)-4-oxo-butyric acid;
4-(2,4-Difluoro-phenyl)-4-oxo-butyric acid;
4-(4-Butoxy-phenyl)-4-oxo-butyric acid;
4-Oxo-4-(4-propyl-phenyl)-butyric acid;
4-Oxo-4-(4-pentyl-phenyl)-butyric acid;
4-(4-Hexyloxy-phenyl)-4-oxo-butyric acid;
4-(2,5-Difluoro-phenyl)-4-oxo-butyric acid;
5-(4-Chloro-phenyl)-5-oxo-pentanoic acid;
6-(3,5-Difluoro-phenyl)-6-oxo-hexanoic acid;
4-Oxo-4-p-tolyl-butyric acid;
6-Oxo-6-phenyl-hexanoic acid;
5-Oxo-5-(4-phenoxy-phenyl)-pentanoic acid;
5-Oxo-5-(3-phenoxy-phenyl)-pentanoic acid; and
7-Oxo-7-(3-phenoxy-phenyl)-heptanoic acid;
and salts thereof; and
a biologically active agent selected from human growth hormone, interferon, insulin, heparin, low molecular weight heparin, cromolyn sodium, PYY, calcitonin, parathyroid hormone, erythropoietin, or any combination thereof.

4. The pharmaceutical composition of claim 1, wherein the biologically active agent comprises insulin.

5. The pharmaceutical composition of claim 1, wherein the biologically active agent comprises heparin.

6. The pharmaceutical composition of claim 1, wherein the biologically active agent comprises low molecular weight heparin.

7. The pharmaceutical composition of claim 1, wherein the biologically active agent comprises PYY or a PYY agonist.

8. The pharmaceutical composition of claim 1, wherein the biologically active agent comprises PYY[3-36].

9. The pharmaceutical composition of claim 1, wherein said biologically active agent comprises parathyroid hormone.

10. A dosage unit form comprising
(A) a pharmaceutical composition of claim 1; and
(B) (a) an excipient
(b) a diluent,
(c) a disintegrant,
(d) a lubricant,
(e) a plasticizer,
(f) a colorant,
(g) a dosing vehicle, or
(h) any combination thereof.

11. A method for administering a biologically active agent selected from human growth hormone, interferon, heparin, low molecular weight heparin, cromolyn sodium, PYY, calcitonin, parathyroid hormone, erythropoietin, and combinations thereof to an animal in need of the biologically active agent, the method comprising administering orally to the animal a pharmaceutical composition of claim 1.

12. A method for preparing a pharmaceutical composition, said method comprising mixing:
(A) at least one biologically active agent selected from human growth hormone, interferon, heparin, low molecular weight heparin, cromolyn sodium, PYY, calcitonin, parathyroid hormone, erythropoietin, and combinations thereof; and
(B) at least one compound of the formula:

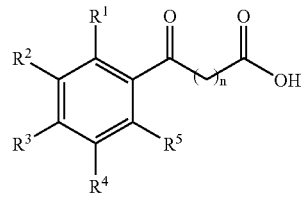

or a salt thereof, wherein
n is an integer from 1 to 9,
$R^2$ to $R^4$ are independently hydrogen, $C_1$ to $C_6$ alkyl, $C_1$ to $C_6$ alkoxy, $C_2$ to $C_6$ alkenyl, halogen, hydroxyl, or —O—$C_6H_5$, and
$R^1$ and $R^5$ are independently hydrogen, $C_1$ to $C_6$ alkoxy, $C_2$ to $C_6$ alkenyl, halogen, or —O—$C_6H_5$,
or a salt thereof.

13. The pharmaceutical composition of claim 1, wherein the delivery agent is selected from:
4-Oxo-4-phenyl-butyric acid;
10-(4-Hydroxy-phenyl)-10-oxodecanoic acid;
4-(4-Methoxy-phenyl)-4-oxo-butyric acid;
5-(4-Methoxy-phenyl)-5-oxo-pentanoic acid;
4-(3,5-Difluoro-phenyl)-4-oxo-butyric acid;
5-Oxo-5-phenyl-pentanoic acid;
5-(4-Isopropyl-phenyl)-5-oxo-pentanoic acid;
4-(2-Methoxy-phenyl)-4-oxo-butyric acid;
4-(4-Fluoro-phenyl)-4-oxo-butyric acid;
6-(4-Methoxy-phenyl)-6-oxo-hexanoic acid;
6-(3,4-Dimethyl-phenyl)-6-oxo-hexanoic acid;
4-(3,4-Dimethyl-phenyl)-4-oxo-butyric acid;
6-(2,5-Dichloro-phenyl)-6-oxo-hexanoic acid;
4-(2,5-Dichloro-phenyl)-4-oxo-butyric acid;
8-Oxo-8-phenyl-octanoic acid;
6-(2,5-Difluoro-phenyl)-6-oxo-hexanoic acid;
7-Oxo-7-phenyl-heptanoic acid;
4-(4-Ethyl-phenyl)-4-oxo-butyric acid;
4-(2,4-Difluoro-phenyl)-4-oxo-butyric acid;
4-(4-Butoxy-phenyl)-4-oxo-butyric acid;
4-Oxo-4-(4-propyl-phenyl)-butyric acid;
4-Oxo-4-(4-pentyl-phenyl)-butyric acid;
4-(4-Hexyloxy-phenyl)-4-oxo-butyric acid;
4-(2,5-Difluoro-phenyl)-4-oxo-butyric acid;
5-(4-Chloro-phenyl)-5-oxo-pentanoic acid;
6-(3,5-Difluoro-phenyl)-6-oxo-hexanoic acid;
4-Oxo-4-p-tolyl-butyric acid;
6-Oxo-6-phenyl-hexanoic acid;
5-Oxo-5-(4-phenoxy-phenyl)-pentanoic acid;
5-Oxo-5-(3-phenoxy-phenyl)-pentanoic acid; and
7-Oxo-7-(3-phenoxy-phenyl)-heptanoic acid;
and salts thereof.

* * * * *